United States Patent [19]

Little et al.

[11] 4,346,699

[45] Aug. 31, 1982

[54] WATER PROOF CAST PROTECTOR

[76] Inventors: John D. Little, 25097 Champlain Rd., Laguna Hills, Calif. 92653; James Z. Cloud, Jr., 1215 S. Athena Way, Anaheim, Calif. 92806

[21] Appl. No.: 248,900

[22] Filed: Mar. 30, 1981

Related U.S. Application Data

[60] Continuation of Ser. No. 100,987, Dec. 6, 1979, abandoned, which is a continuation of Ser. No. 909,967, May 26, 1978, abandoned, which is a continuation-in-part of Ser. No. 784,496, Apr. 4, 1977, Pat. No. 4,139,003, which is a division of Ser. No. 636,508, Dec. 1, 1975, Pat. No. 4,034,326, which is a continuation of Ser. No. 530,959, Dec. 9, 1974, abandoned.

[51] Int. Cl.³ .............................................. A61F 13/00
[52] U.S. Cl. ..................................................... 128/82
[58] Field of Search ........................... 128/82, 83, 157

[56] References Cited

U.S. PATENT DOCUMENTS 835,803  11/1906  Witten ................................. 128/157

OTHER PUBLICATIONS

"Derma-Tectors", Journal American Medical Assoc., vol. 117, No. 18, Nov. 1941, p. 26.

*Primary Examiner*—John D. Yasko
*Attorney, Agent, or Firm*—Knobbe, Martens

[57] ABSTRACT

A flexible covering for placing over an individual's injured limb having a cast or bandage. The covering consists of a tubular piece of flexible material, one end of which is open and the other end of which is closed in a receptacle for the hand or foot of the individual. The tube tapers into a neck at its open end so as to provide a sealing portion which snugly engages the limb of the individual above the upper termination of the cast or bandage. The sealing portion or neck has an interior diameter smaller than the diameter of the limb above the cast or bandage in order to provide a sealing engagement with the limb. The covering is designed for use by the individual with the injured limb when he is bathing in order to protect the cast or bandaged area from contact with water.

1 Claim, 5 Drawing Figures

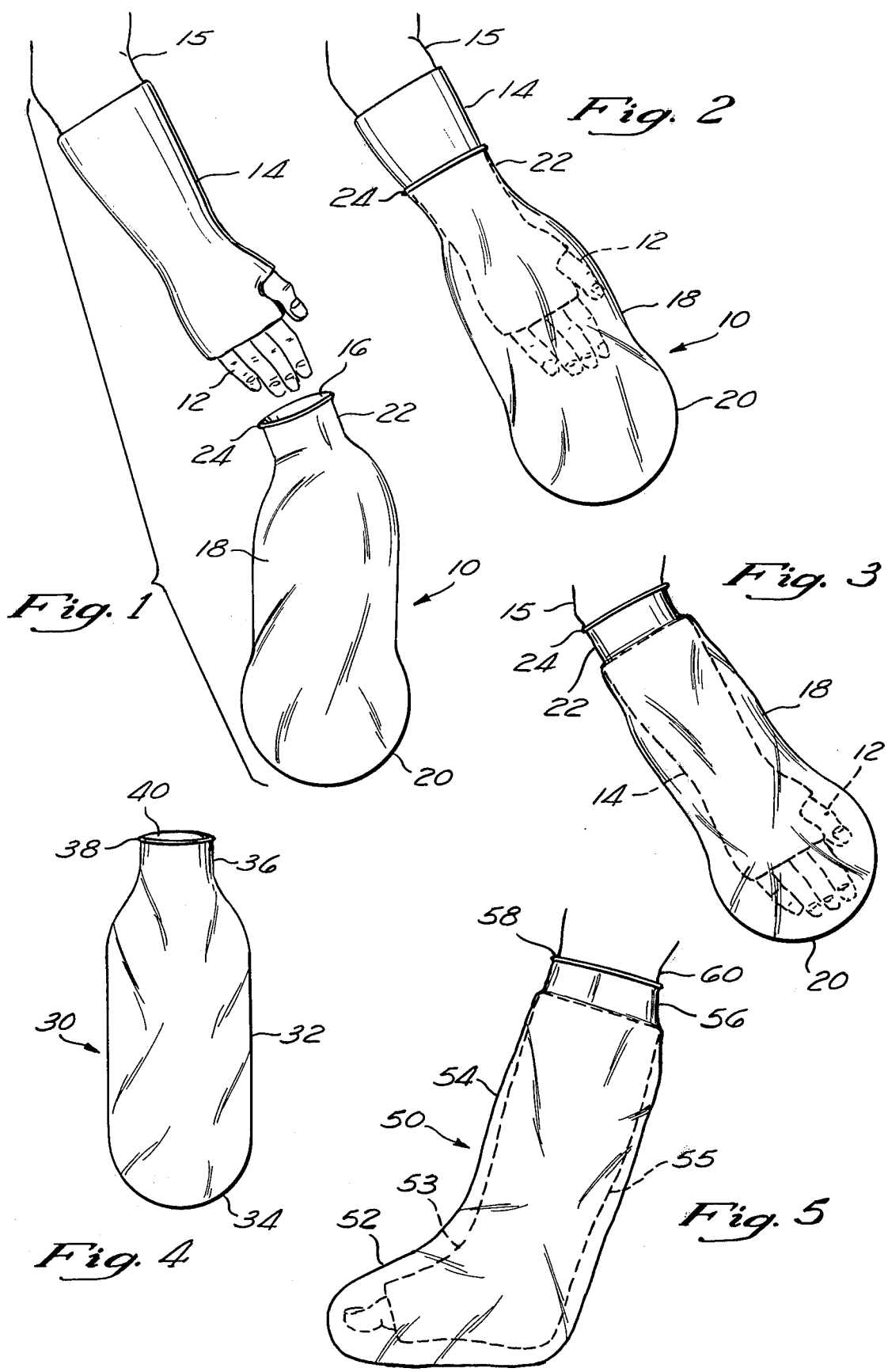

WATER PROOF CAST PROTECTOR

CROSS-REFERENCES TO RELATED APPLICATIONS

This application is a continuation of application Ser. No. 100,987, filed Dec. 6, 1979, now abandoned, which, in turn, is a continuation of U.S. patent application, Ser. No. 909,967, filed May 26, 1978, now abandoned, which is a continuation-in-part of co-pending U.S. patent application, Ser. No. 784,496, filed Apr. 4, 1977, now U.S. Pat. No. 4,139,003, which is a divisional application of U.S. patent application, Ser. No. 636,508, filed Dec. 1, 1975, now U.S. Pat. No. 4,034,326, which is a continuation of U.S. patent application, Ser. No. 530,959, filed Dec. 9, 1974, now abandoned.

BACKGROUND OF THE INVENTION

This invention relates to the field of protective coverings for injured areas of individuals and more specifically relates to a covering which is designed to provide protection to a cast or bandage on the limb of the individual while the individual is bathing. One of the most frustrating situations for an individual who has a cast on his arm or leg is the inability to bath normally using a shower or bath because of the danger of water damage to the cast or the bandaged area. Consequently, the individual is forced to utilize the co-called sponge bath which is more time consuming and more inconvenient, rendering a less than adequate job of cleansing.

In the prior art, the typical approach for an individual who desires to take a shower with a cast is to place a plastic-type bag over his leg or arm and to secure it by tying it or placing a rubber band around the upper portion right above the cast or bandaged area. Although this sometimes provides satisfactory sealing, the seal in most instances is not proper and will result in some moisture entering the cast or bandaged area. Furthermore, the individual whose has one arm in the cast does not have the dexterity adequately to tie or seal the upper portion of the bag over the top of the cast on the opposite arm. Typically, water proof protectors used for patients having a cast when bathing have been the homemade type which are generally inadequate for sealing moisture from the cast, and also require the aid of a second individual to help in the placement of the covering over the cast.

SUMMARY OF THE INVENTION

The present invention comprises a unitary flexible covering in the form of an elongate bag having a length sufficient to cover the entire length of the cast or bandaged area. The closed end of the bag forms a receptacle for receiving the foot or hand of the injured limb and the portion of the bag which covers the cast or bandaged area has an inside diameter which is large enough to fit loosely over the cast or bandaged area, forming a water proof protective covering for this portion of the limb. The bag tapers into a short relatively narrow neck at the open end, and formed around the opening at the terminus of the neck is a ridge or rib. The neck fits around the portion of the limb immediately above the termination of the cast or bandaged area and has an inside diameter which is slightly smaller than that of the limb so that a snug sealing water-tight fit is effected against the limb. The hand or foot is inserted into the opening and the bag is pulled up over the hand or foot and over the cast or bandaged area until the narrow neck is above the cast or bandaged area where it fits snugly against the skin on the limb above the cast, maintaining a tight seal to prevent the entrance of any water into the injured area of the limb. The rib or ridge around the opening facilitates the pulling of the covering on and off of the limb and also prevents the edges of the bag around the opening from rolling up when the covering is in place.

The covering device is designed to allow easy application and removal by the temporarily handicapped individual, often eliminating the need for additional help when placing the covering over the cast, since with an arm cast covering, for example, he can easily apply the covering by use of his free arm. The device is designed to be disposable after use and can easily be removed by simply pulling or rolling the neck down over the cast area and off of the hand or foot. Also, the device may be simply cut with a scissors for easy removal.

The invention thus provides the individual with a covering device that is inexpensive and easy to apply, allowing the individual to maintain his ability to bathe in a normal fashion and alleviating much of the inconvenience associated with having a cast or heavily bandaged arm or leg.

BRIEF DESCRIPTION OF THE DRAWINGS

FIG. 1 is a perspective view of the preferred arm embodiment of the invention prior to application on an individual's arm having a cast;

FIG. 2 is a perspective view of the preferred arm embodiment of the invention in the process of being pulled over the cast on the individual's arm;

FIG. 3 is a perspective view of the preferred arm embodiment of the invention completely covering the cast on the arm and sealingly engaged against the skin of the arm above the cast;

FIG. 4 is a perspective view of an alternative arm embodiment of the invention; and FIG. 5 is a perspective view of the leg embodiment of the invention in place over a cast on an individual's leg.

DETAILED DESCRIPTION OF THE INVENTION

Referring first to FIG. 1, the preferred arm embodiment of a cast procedure in accordance with the present invention is shown generally at 10 in its previous configuration and ready for placement over an individual's hand 12, arm cast 14 and arm 15. The cast protector 10 is in the form of an elongate bag of flexible stretchable water proof material, preferably latex. One end of the bag is provided with an opening 16. The major portion of the length of the cast protector bag 10 consists of a cast covering portion 18 which has an inside diameter which is larger than the outside diameter of the cast 14 so that the cast covering portion 18 may fit losely around the cast 14. The end of the cast covering portion 18 opposite the openings 16 terminates in an enlarged bulbous closed receptacle portion 20 for receiving and enclosing the hand 12. At the end of the cast covering portion 18 opposite the receptacle portion 20, the cast protector bag 10 is tapered rather abruptly to form a relatively short narrow neck or sealing portion 22 which is terminated by a flexible stretchable sealing ring or rib 24 around the opening 16. The inside diameter of the neck or sealing portion 22 is substantially uniform, and smaller than the portion of the arm 15 above the cast 14 so that the neck 22 will form a snug water proof sealing engagement against the skin of the arm 15. In FIG. 2 the cast protector is shown during the process of being pulled up over the cast 14. The hand 12 has been inserted into the opening 16 and the cast protector bag 10 has been pulled part way up the cast 14. The neck 22 and the stretchable rib 24 stretch to accommodate the diameter of the cast 14 which is considerably greater than the inside diameter of the neck 22 and the rib 24. The rib 24 facilitates the gripping of the device so as to aid in pulling the neck 22 up over the cast 14. Furthermore, the rib 24 provides greater tensile strength to the material around the opening 16 so as to prevent tearing during the pulling-on process. The relative shortness of the neck 22 minimizes the amount of material that must be stretched in being pulled over the cast, thereby facilitating the application of the device.

FIG. 3 shows the cast protector bag 10 fully in place over the cast 14. In this position the hand 12 is comfortably and loosely enclosed in the receptacle portion 18 while the cast covering portion 20 losely covers the cast 14. The neck or sealing portion 22 has been pulled up over the upper end of the cast 14 where it fits in a snug water tight sealing engagement against the skin of the arm 15 due to the fact that the relaxed inside diameter of the neck 22 is slightly smaller than the diameter of the arm 15 as previously mentioned. The sealing rib or ring 24, which is also smaller in diameter than the arm 15, also snugly engages against the skin of the arm and serves the further purpose of inhibiting the rolling up of the material around the opening 16. Moreover, the ring or rib 24 enhances the water tight sealing of the neck 22 around the arm 15 to prevent the entrance of moisture into the cast protector 10.

With the cast protector 10 fully applied as shown in FIG. 3, the individual can enter a shower or bath and bath himself without causing any water damage to the cast or to the bandaged arm. When the bath or shower is finished, the individual may simply grasp the cast protector about the rib 24 with his free hand and simply pull the device down over the cast and off of his hand.

It will be readily noted that the enlarged bulbous receptacle portion 20 of the preferred arm embodiment of the invention provides ample room to accommodate a cast or bandage which is applied to the hand 12 of the individual. In cases where the hand is not bandaged or in a cast, an alternative arm embodiment of the invention, as illustrated in FIG. 4, may be conveniently used. In this alternative arm embodiment, a cast protector bag shown generally at 30 comprises an essentially straight tubular cast covering section 32 having a rounded closed end 34. As in the preferred embodiment, the cast covering portion 32 has a relaxed inside diameter which is substantially larger than the outside diameter of the cast so that it fits losely around the cast. The closed rounded end portion 34 is large enough to accommodate an unbandaged hand. As in the preferred arm embodiment, the alternative embodiment cast protector bag 30 abruptly tapers to a relatively short narrow neck or sealing portion 36, which has a substantially uniform diameter, terminating in a resilient flexible rib or ring 38 around a bag opening 40. Again, the neck or sealing portion 36 and the rib or ring 38 have relaxed inside diameters which are smaller than the diameter of the portion of the arm above the cast so that a snug water tight engagement may be made against the skin of the arm. The cast protector 30 is applied and removed exactly as is the preferred embodiment.

Similar protection for the leg of an individual is afforded by the leg embodiment of the invention illustrated in FIG. 5 and indicated generally at 50. The leg cast protector 50 is proportionately larger than the arm cast protector and is similar to the arm cast protector in all material respects with the exception of the closed end which in the case of the leg cast protector 50 is in the form of a generally foot-shaped receptacle 52 which joins the remainder of the cast protector bag at an angle which approximates the angle between a human foot and leg, and which is large enough to accommodate loosely a foot 53 having a bulky cast or bandage. The major portion of the length of the leg cast protector 50 above the foot receptacle portion 52 comprises an essentially tubular cast covering portion 54 which has a relaxed inside diameter which is substantially larger than that of a leg cast 55 so that the cast covering portion 54 fits losely about the cast. As with the arm embodiments of the invention the leg cast protector bag 50 rather abruptly tapers above the cast covering portion 54 into a relatively short, substantially uniform diameter, narrow neck or sealing portion 56 terminated by a stretchable flexible sealing ring 58 around the bag opening (not shown). Again, the relaxed inside diameters of the neck or sealing portion 56 and the sealing ring or rib 58 are somewhat smaller than the diameter of the bare portion of an individual's leg 60 above the cast. Thus, as shown in FIG. 5 with the leg cast protector bag 50 fully applied on the leg 60 of an individual, the neck 56 and the rib 58 effect a snug water tight sealing engagement against the bare skin of the leg 60 above the cast. The application and removal of the leg cast protector 50 is analogous to that of the arm cast protector previously discussed.

By way of specific examples, an arm cast protector designed to accommodate a half arm cast on an average sized adult arm is preferably made with an overall length of approximately twenty inches, of which approximately one and one-half inches comprises the length of the neck 22. The relaxed inside diameters of the cast covering portion 18 and the neck 22 are approximately eight inches and four and one-eighth inches respectively, while the maximum relaxed diameter of the bulbous hand receptacle portion 20 is approximately nine inches. A leg cast protector for a full-leg cast on an average adult leg would have an overall length of approximately forty inches of which approximately one and one-half inches comprises the length of the neck 56. A foot receptacle portion 52 has a heel-to-toe length of approximately fifteen inches and a maximum relaxed width of approximately ten inches. The relaxed inside diameter of the neck 56 is approximately six inches, while the cast covering portion 54 has a relaxed inside diameter of approximately thirteen inches at the top, gradually decreasing to approximately nine and three quarters inches at the juncture with the foot receptacle portion 52.

Cast protectors manufactured with the above described dimensions have been determined to be able to fit losely around arm and leg casts and bandages in the usual range of thicknesses, while effecting a snug water tight sealing engagement with the limb above the cast or bandage which is not overly tight or constrictive. It should be noted that the above dimensions can be varied to accommodate the limbs of children of different ages and adults of different sizes. Furthermore, the arm cast protector can be made substantially longer so as to accommodate a full-arm cast or substantially shorter to accommodate a cast which covers only the hand or wrist of the individual. Likewise, the leg cast protector can be made substantially shorter to accommodate a cast which covers only the lower part of the individual's leg, as illustrated in FIG. 5.

What is claimed is:

1. A protective covering to seal a cast or bandage on the individual's arm or leg from water in bathing comprising:
   - a tubular cast covering portion of flexible, resilient material, having an inside diameter larger than the outside diameter of said cast or bandage;
   - a closed receptacle portion of flexible, resilient material integral with one end of said cast covering portion, having an inside diameter larger than the outside diameter of said cast or bandage and adapted to enclose the hand or foot of the individual;
   - a tubular sealing portion of flexible, resilient material having one end integral with the other end of said cast covering portion, the other end of said sealing portion being open, said sealing portion having a substantially uniform diameter substantially less than the diameter of said cast covering portion, said sealing portion being of an extended length sufficient to form a watertight seal around a section of the arm or leg, said arm or leg section being located above the upper termination of said cast and having a diameter which varies considerably along its length; and
   - a flexible, stretchable rib around said open end of the sealing portion to provide strength to said sealing portion and enhance the watertight seal.

* * * * *